(12) United States Patent
Speier et al.

(10) Patent No.: US 11,096,630 B2
(45) Date of Patent: Aug. 24, 2021

(54) GENERATING A MOVEMENT SIGNAL OF A PART OF THE HUMAN OR ANIMAL BODY

(71) Applicant: Siemens Healthcare GmbH, Erlangen (DE)

(72) Inventors: Peter Speier, Erlangen (DE); Mario Bacher, Nuremberg (DE)

(73) Assignee: Siemens Healthcare GmbH, Erlangen (DE)

( * ) Notice: Subject to any disclaimer, the term of this patent is extended or adjusted under 35 U.S.C. 154(b) by 470 days.

(21) Appl. No.: 16/003,837

(22) Filed: Jun. 8, 2018

(65) Prior Publication Data
US 2018/0353140 A1 Dec. 13, 2018

(30) Foreign Application Priority Data

Jun. 8, 2017 (DE) .................. 102017209710.8
Jul. 5, 2017 (EP) ..................... 17179814

(51) Int. Cl.
*A61B 5/055* (2006.01)
*A61B 5/00* (2006.01)
(Continued)

(52) U.S. Cl.
CPC ............ *A61B 5/7289* (2013.01); *A61B 5/055* (2013.01); *G01R 33/5673* (2013.01);
(Continued)

(58) Field of Classification Search
CPC ..... A61B 5/055; A61B 5/4504; A61B 5/7289; G01R 33/56509; G01R 33/5676; G01R 33/56308; G01R 33/5673
See application file for complete search history.

(56) References Cited

U.S. PATENT DOCUMENTS 7,702,376 B2   4/2010  Frank et al.
7,899,521 B2   3/2011  Demharter et al.
(Continued)

FOREIGN PATENT DOCUMENTS

DE     102015224162      6/2017

OTHER PUBLICATIONS

Eigendecomposition of a matrix, in: https://en.wikipedia.org/wiki/Eigendecomposition_of_a_matrix, May 7, 2017.
(Continued)

*Primary Examiner* — Mark D Remaly
(74) *Attorney, Agent, or Firm* — Lempia Summerfield Katz LLC

(57) ABSTRACT

A method for generating a movement signal of a body part, of which at least a portion is undergoing a cardiac movement, includes providing a pilot tone signal acquired from the body part by a magnetic resonance receiver coil arrangement. A demixing matrix is calculated from a calibration portion of the Pilot Tone signal using an independent component analysis algorithm. The independent component corresponding to the cardiac movement is selected. The demixing matrix is applied to further portions of the pilot tone signal to obtain a movement signal representing the cardiac movement. An, adaptive stochastic, or model-based filter is applied to the signal representing the cardiac movement, to obtain a filtered movement signal.

20 Claims, 5 Drawing Sheets

(51) Int. Cl.
*G01R 33/563* (2006.01)
*G01R 33/567* (2006.01)
*G01R 33/565* (2006.01)

(52) U.S. Cl.
CPC ... *G01R 33/5676* (2013.01); *G01R 33/56308* (2013.01); *G01R 33/56509* (2013.01)

(56) References Cited

U.S. PATENT DOCUMENTS

| | | | |
|---|---|---|---|
| 8,116,856 | B2 | 2/2012 | Roβler |
| 2007/0253599 | A1* | 11/2007 | White .............. G01R 33/56509 382/107 |
| 2008/0039708 | A1* | 2/2008 | Taicher .................. A61B 5/055 600/410 |
| 2016/0245888 | A1 | 8/2016 | Bollenbeck et al. |
| 2017/0160364 | A1 | 6/2017 | Fenchel et al. |

OTHER PUBLICATIONS

EPO Search Report 02132018, cited in corresponding European Patent Application No. 17179814.3; dated Feb. 13, 2018, 11 pages.
Extended Kalman filter, in: https://en.wikipedia.org/wiki/Extended_Kalman_filter, May 7, 2017.
FastICA, in: https://en.wikipedia.org/wiki/FastICA, May 7, 2017.
Hidden Markov model, in: https://en.wikipedia.org/wiki/Hidden_Markov_model, May 7, 2017.
I. Graesslin et al., Advancements in contact-free Respiration Monitoring using RF Pick-up coils, ISMRM 2010, Traditional Poster.; 2010.
Independent component analysis, in: https://en.wikipedia.org/wiki/Least_mean_squares_filter, May 7, 2017.
Infomax, in: https://en.wikipedia.org/wiki/Infomax, May 7, 2017.
Jaeschke S.H.F. et al., Contact-free Cardiac Motion Estimation using the Scatter of a Parallel Transmit Coil at 7T MRI, Proceedings of the 25th Annual Meeting of ISMRM, Honolulu, Hawaii, USA, Apr. 22-27, 2017, No. 3262, pp. 3262, XP040690830; 2017.
Johnson, C.C. et. al., Nonionizing Electromagnetic Wave Effects in Biological Materials and Systems, in: Proceedings of the IEEB, vol. 60, No. 6, 1972, pp. 692-718.
Kalman filter, in: https://en.wikipedia.org/wiki/Kalman_filter, May 7, 2017.
Kim, S. et. al., Multiharmonic Frequency Tracking Method Using The Sigma-Point Kalman Smoother, in: EURASIP Journal on Advances in Signal Processing, 2010, Article ID 467150, doi:10.1155/2010/467150.
Least mean squares filter, in: https://en.wikipedia.org/wiki/Least_mean_squares_filter, May 7, 2017.
MLSP-Lab—Machine Learning for Signal Processing Laboratory, in: http://mlsp.umbc.edu/ica_ebm.html, May 7, 2017.
Pascal Spincemaille et al, Kalman filtering for real-time navigator processing, Magnetic Resonance in Medicine., vol. 60, No. 1, pp. 158-168, XP055447072, US ISSN: 0740-3194, DOI: 10.1002/mrm.21649; 2008.
Pfanner F. et. al., Monitoring cardiac motion in CT using a continuous wave radar embedded in the patient table, in: Medical Physics, vol. 41, No. 8. Aug. 2014.
Principal component analysis, in: http://en.wikipedia.org/wiki/Principal_component_analysis, May 7, 2017.
Schroeder, L. et. al., Novel Method for Contact-Free Cardiac Synchronization Using the Pilot Tone Navigator, in: proceedings of the 24th Annual Meeting of the ISMRM, Singapur, 7.-13.5.2016, pp. 410, 2016.
Schroeder, L. et. al., Two-Dimensional Respiratory-Motion Characterization for Continuous MR Measurements Using Pilot Tone Navigation, in: Proceedings of the 24th Annual Meeting of the ISMRM (ISMRM 2016), Singapur, 7.-13-5.2016, pp. 3103.
Singular value decomposition, in: https://en.wikipedia.org/wiki/Singular_value_decomposition, May 7, 2017.
Wetzl, J. et. al., Feasibility Study: Free-Breathing 3-D CINE Imaging with Respiratory Gating Based on Pilot Tone Navigation, in: Proceedings of the 24th Annual Meeting of the ISMRM (ISMRM 2016), Singapur, 7.-13.5.2016, pp. 3103.
Pfanner, Florian, et al. "Monitoring internal organ motion with continuous wave radar in CT." Medical physics 40.9 (2013): 091915.

\* cited by examiner

GENERATING A MOVEMENT SIGNAL OF A PART OF THE HUMAN OR ANIMAL BODY

This application claims the benefit of German Patent Application No. DE 10 2017 209 710.8, filed on Jun. 8, 2017, and European Patent Application No. EP17179814.3, filed on Jul. 5, 2017, which are hereby incorporated by reference in their entirety.

BACKGROUND

The present embodiments relate to generating a movement signal of a part of a human or animal body.

Patient movement or motion during a diagnostic examination or scan of medical data (e.g., during radiological imaging) often causes artefacts in the acquired images. Magnetic resonance (MR) imaging is relatively slow, so that respiratory and cardiac movement will occur during the scan. If the movement is known, the data acquisition may be triggered to a particular phase in the cyclical movement, or the acquired data may be corrected. It is therefore common practice to acquire an electrocardiogram (ECG) of the patient during radiological imaging in order to trigger the data acquisition to a particular phase in the cardiac cycle. For example, U.S. Pat. No. 8,116,856 B2 or U.S. Pat. No. 7,899,521 B2 describe an arrangement for recording ECG signals, and U.S. Pat. No. 7,702,376 B2 describes a method for ECG-triggering a measuring sequence of a magnetic resonance device. However, taking an ECG during an MR scan presents difficulties, for example, because of the high magnetic fields, which may cause interferences in the ECG leads. Therefore, other methods of detecting patient movement (e.g., cardiac movement) during a radiological scan are to be provided.

An innovative way for inferring information about respiratory motion or patient motion during patient acquisitions in MR measurements, termed "pilot tone (PT) navigation" has been described in DE 10 2015 224 162 A1, which is hereby incorporated by reference in its entirety.

The basic principle is to measure the variation induced by physiological motion using a coherent or continuous external frequency signal received by the local coil elements outside the receive bandwidth of the actually scanned MR field of view, but within the range of the oversampling bandwidth that is acquired during every readout.

Pfanner et al. describe a similar method based on continuous wave radar, operating in the 860 MHz band and were able to clearly detect and extract cardiac motion from the received signal. However, Pfanner et al. find the signal to be highly dependent on receiver placement, likely due to the short wavelength (e.g., 35 cm in air, less in biological tissues by a factor of about 7). The heart moves during the respiratory cycle and at this small wavelength, this movement is resolved as well. The pilot tone method operates at much larger wavelengths of 4.7 m or 2.3 m in air at 1.5 T and 3 T, respectively, and therefore, may not resolve small movements. Instead, the PT signal is primarily modulated by the volumetric contraction of the heart.

The ability of Pilot Tone navigation to detect physiological motion was previously shown for the respiratory component in Schroeder et al., Wetzl et al., and for the cardiac component, in Schroeder et al. The database may be limited to a handful of measurements with one volunteer; therefore, no conclusions about robustness of the method and required processing to stabilize the signal in various situations may be derived.

SUMMARY AND DESCRIPTION

The scope of the present invention is defined solely by the appended claims and is not affected to any degree by the statements within this summary.

The present embodiments may obviate one or more of the drawbacks or limitations in the related art. For example, a method for robust and real-time processing of a pilot tone signal in order to reliably extract a cardiac movement signal, and separate the cardiac movement signal from other motion and signal components is provided. As another example, synchronization information is extracted from the pilot tone signal (e.g., the information to be provided for prospective triggering and retrospective gating of the imaging data).

One or more of the present embodiments are directed to a method for generating a movement signal of a part of a human or an animal body, of which at least a portion is undergoing a cyclical movement (e.g., a cardiac and/or respiratory movement). The method includes providing a pilot tone signal acquired from the body part by a magnetic resonance receiver coil arrangement including a plurality of channels. The Pilot Tone signal includes a plurality of signal components associated with the plurality of channels. From a calibration portion of the Pilot Tone signal, a demixing matrix is calculated using an independent component analysis (ICA) algorithm, where the demixing matrix calculates the independent components from the plurality of signal components. The independent component(s) corresponding to at least one particular movement type (e.g., the cardiac movement) are selected. The demixing matrix is applied to the further portions of the pilot tone signal to obtain at least one movement signal representing one particular movement type (e.g., the cardiac movement). An adaptive, stochastic, or model-based filter is applied to the at least one movement signal representing one particular movement type (e.g., the cardiac movement) to obtain a filtered movement signal.

The method allows the cardiac motion signal (which is then the movement signal representing one particular movement type) to be reliably extracted with the help of a pilot tone measurement system, and separates the cardiac motion signal from other motions and signal components.

The method may be carried out during a scan of medical data (e.g., medical image data) from the part of the human or animal body (e.g., body part) (e.g., during a magnetic resonance scan). The method may be performed during the whole time of the scan or only during one or several stages of the scan.

One or more of the present embodiments provide a method for filtering and analysis of curve properties, and/or for a segmentation of the movement signal representing the cardiac movement (e.g., cardiac component or cardiac component trace), either in real-time or retrospectively. The method provides a basis for extracting features from the cardiac component, which may be used, for example, for triggering the acquisition of the scan of medical data (e.g., for triggering a magnetic resonance imaging or spectroscopy scan).

One or more of the present embodiments have the advantage of providing reliable ECG-free cardiac imaging. In comparison with known ECG-based imaging methods, one or more of the present embodiments may be implemented at lower costs. Further, since no leads are to be attached to the patient, there is better patient comfort, and the preparation time for the radiological examination is reduced. In addition, the method is more reliable than ECG, because there is no interference between the pilot tone signal and the MR signal, and thus provides increased triggering reliability.

Contrary to ECG-based triggering, the method of one or more of the present embodiments allows a synchronization of the scan of medical data to arbitrary cardiac phases.

The method may be used outside of MR in connection with other imaging or therapy modalities such as PET, SPECT, X-Ray, CT, etc. if the transmitting and receiving hardware for the pilot tone signal (e.g., a receiving coil arrangement) is built as a stand-alone device, independent of the MR scanner hardware.

The part of the human or animal body (e.g., body part), of which at least a portion is undergoing a cyclical movement, may be the organ or body part undergoing a diagnostic examination such as a scan of medical image data (e.g., a heart, blood vessel, thorax, or lung) or another organ affected by motion such as cardiac movement. The scan of medical data or image data may be a magnetic resonance (MR) scan, but may be another modality, such as Positron Emission Tomography (PET), X-Ray, Single Photon Emission Computed Tomography (SPECT), or Computed Tomography (CT). "Cyclical movement" may be that the movement is repeating itself, such as respiration or cardiac movement. The movement is not to be completely rhythmic, as would be impossible for physiological movements. The method may be applied to patients with arrhythmia or irregular respiration as well. The method may also be applied in non-cyclic movements, such as respiratory motion when breathholds are used during the scan, or when the breathing is arrhythmic due to medical conditions.

The Pilot Tone (PT) signal is a frequency signal received by a magnetic resonance receiver coil arrangement (e.g., a standard MR local coil) that has a plurality of channels, outside the receive bandwidth of an MR scan of the body part. The PT signal may be generated by an independent continuous-wave radio frequency (RF) source. The frequency of the emitted PT signal may be between about 20 to 200 kHz away from the center frequency of the Magnetic Resonance receiver coil arrangement (e.g., of the MR scanner) to avoid interference with the desired Magnetic Resonance imaging (MRI) data, but still within the application imaging bandwidth. The center frequency is, for example, 123.2 MHz at 3 T. In other embodiments, the frequency of the emitted PT signal is outside the application imaging bandwidth but still inside the range digitized in the receiver. In that case, the frequency may be in the range of 1-5 MHz (e.g., at one half of the Nyquist frequency).

Since the frequency range of the PT signal does not cover the Larmor frequency, the received PT signal is unaffected by MR effects. However, the PT signal is modulated by the movement of the body part, since this movement influences the signal transmission between the source and the receiver coil arrangement, and may affect the load and therefore the receive characteristics of the receiver coil arrangement.

An MR receiver coil arrangement may include a plurality of elements (e.g., in the form of a coil array), each acquiring a separate signal component. In other words, the PT signal includes a plurality of signal components (e.g., complex) received from a plurality of channels. In one embodiment, 4 to 128 (e.g., 8 to 64) receiver channels are used, as are used in modern MR receiver coil arrangements. Different types of movement may affect the channels to different degrees, depending, for example, on the orientation and position of the moving body part with respect to the coil element. The signal components of the PT signal are to be combined in an intelligent way in order to extract particular movement types such as cardiac movement and/or respiratory movement.

A "Movement type" provides one of several motion types happening in the body part at the same time (e.g., cardiac movement, respiratory movement, and other voluntary or involuntary patient movement such as turning of head, moving of hand or legs etc.). The method of one or more of the present embodiments may be particularly applied to extract the cardiac movement, but may be used to extract any other movement type as well. A "cardiac movement" provides any movement caused by the regular contraction of the heart muscles (e.g., in the heart itself or in other body parts affected by the contraction, such as by arterial blood vessels).

In one embodiment, respiratory motion is detected alongside cardiac motion. Thus, even if the respiratory motion of the heart introduces some small error (e.g., at higher field strengths where the pilot tones signal is to be of higher frequency (298 MHz at 7 T)), this error may be accounted for knowing the respiratory signal. The respiratory signal/component may be detected in the same way as the cardiac component (e.g., as an independent component of the pilot tone signal). This may be done by independent component analysis (ICA), as described in detail below. Alternatively, any errors introduced by respiratory motion may be corrected with a respiration resolved training (e.g., instead of applying and training a single template or a single adaptive, stochastic, or model-based filter to the signal representing the cardiac movement, a series of templates or filters are trained, which vary with the respiratory phase). Thus, these different filters are applied to the signal representing the cardiac movement, depending on the respiratory phase.

The pilot tone signal may be acquired during the entire scan of medical data (e.g., a magnetic resonance scan), and thus, the method of one or more of the present embodiments may be used to generate a movement signal over the entire scan of medical data, or at least relevant parts thereof.

The pilot tone signal may undergo a calibration and possibly other pre-processing acts, examples of which are described below. One or more of the present embodiments focus on the next processing act, in which a movement signal relating to one particular movement is separated from the PT signal components, and the subsequent filter act allowing certain features in the movement signal to be detected.

As part of the processing act, a demixing matrix is calculated from a calibration portion of the pilot tone signal by an independent component analysis (ICA). The ICA is performed on the several signal components corresponding to the plurality of channels. A demixing matrix generally separates the independent components (e.g., corresponding to different movement types) from a plurality of signal components. In this case, the demixing matrix, which is applied to the further portions of the pilot tone signal, is a demixing matrix when extracting a plurality of movement types, but becomes a demixing vector when only one movement type (e.g., independent component) is extracted. Thus, the term "demixing matrix" may also cover "demixing vector", depending on whether one or several movement types are extracted. The demixing matrix, when applied to the pilot tone signal, will separate at least one particular movement type (e.g., the cardiac component) from the several signal components. Depending on the implementation of the ICA, this demixing matrix may be either complex or real-valued.

In one or more of the present embodiments, ICA is first used to extract a plurality of independent components from a calibration portion of the Pilot Tone signal, and when the independent component(s) corresponding to the desired movement types have been selected, a demixing matrix or vector that extracts these movement type(s) is applied to the further portions of the Pilot Tone signal (e.g., in real time). When several movement types are to be extracted, applying the demixing matrix may result in a plurality of movement signals, each representing one particular movement type.

The "calibration portion" of the pilot tone signal may be a short portion covering only a few (e.g., 1 to 20) heartbeats acquired before or at the beginning of the scan of medical data.

Alternatively, where, for example, the movement signal is to be applied retrospectively, the calibration portion may cover the complete or a part of the pilot tone signal (e.g., the complete pilot tone signal acquired during the scan). In other words, ICA may be done either retrospectively on the whole signal acquired during the scan or, for real-time triggering applications, following a short calibration scan. The computed demixing matrix may then be used to unmix incoming data in real-time.

Since any motion by the patient affects the load of the coil elements in a potentially unpredictable way, the following acts relating to the ICA are important to extract the signal components of the desired movement type (e.g., cardiac motion) from the overall pilot tone signal. Any unwanted patient motion like turning the head, feet, etc. may affect the overall signal by adding offsets to the coil elements. The goal is to compute an optimal linear channel combination, which would weigh the contributions of the different channel elements accordingly (e.g., suppressing contributions from unwanted patient motion while maximizing sensitivity to one particular movement type such as cardiac motion).

One way to obtain an ideal channel combination is to apply independent component analysis (ICA), either on real valued or complex data. ICA is based on the assumption that individual components of a multivariate signal are non-Gaussian and that the individual components are statistically independent from each other. ICA finds the independent components by maximizing the independence of the estimated components. Statistical independence may generally be achieved by either minimizing the mutual information or by maximizing the non-gaussianity. Thus, solving the ICA may be formulated as a minimization or maximization problem, depending on the measure of statistical independence used and solved by a variety of minimization techniques (e.g., gradient descent methods or the Gauss-Newton algorithm and corresponding variants).

Several algorithms exist for performing ICA, either in the complex or real domain (e.g., Infomax, FastICA, or Entropy-Bound-Minimization (EBM) and Entropy-Rate-Bound-Minimization (ERBM)). As mentioned above, the respiratory motion of the heart may be an issue at higher field strengths, especially at 7 T. However, ICA may be able to separate this respiratory movement component from the component generated by the pumping action of the heart.

The demixing matrix may be computed only once (e.g., in the beginning of the scan of medical data). However, unwanted motion of the patient after the demixing matrix has been computed may result in a degradation of separation quality, especially during longer scans. In this case, the demixing matrix may be updated iteratively in either regular or irregular intervals during the scan (e.g., whenever an unwanted patient movement has been detected). Thus, the act of calculating a demixing matrix may be repeated in either regular or irregular intervals during the scan. The recalculation may be triggered by analyzing the PT or MR signal.

ICA generally may not identify the actual number of source signals (e.g., independent components), ordering, and scaling (e.g., including sign). Therefore, the choice of the right independent component (e.g., the component containing cardiac motion) may be done either manually by the operator, or by computing quality criteria from the independent components, such as the signal energy in the frequency band that is characteristic for the particular movement type. Selected manually provides that a user or an operator may select the independent component with the help of a user interface. The quality criterion may be the signal energy in the cardiac motion band (e.g., 0.5-6 Hz) over signal energy in other frequency bands, correlation to a given, a priori template of a typical cardiac motion signal, wavelet analysis with a suitable wavelet, or correlation to an imaging navigator signal acquired during a short calibration scan. Thus, the independent component corresponding to the cardiac movement may be selected by computing quality criteria such as mentioned above for each independent component calculated by the demixing matrix, and selecting that independent component having a quality criterion that is closest to that of the desired movement type. For example, the independent component with has most signal energy in the cardiac frequency band is selected.

Once the demixing matrix has been obtained (e.g., using a short calibration scan preceding the scan of medical data, followed by independent component analysis, as described above, incoming data like the further portions of the pilot tone signal, or the complete or part of the pilot tone signal acquired during the scan of medical data, is multiplied with the demixing matrix/vector. By selecting the correct independent component, a movement signal relating to one particular movement type (e.g., cardiac movement) is obtained.

In a next act, the cardiac component is further processed by filtering (e.g., in real-time) to, for example, obtain triggers.

Accordingly, an adaptive, stochastic, or model-based filter is applied to the signal representing one particular movement type (e.g., the cardiac movement, in the following, referred to as cardiac component) to obtain a filtered movement signal. The filter may be, for example, a Kalman filter, an extended Kalman filter, or a switched Kalman Filter.

The filter may have to fulfil the following criteria: If the filtered movement signal is to be used in triggering, the filter may not introduce significant delay. Therefore, advanced filters like adaptive, stochastic, or model-based filters are to be provided. In one embodiment, the filter not only suppresses noise of the cardiac component, but may also provide information about the relevant trigger points. This is relevant, for example, for cyclical movements like the cardiac movement, where it may be desired to trigger a scan of medical data to one particular physiological phase of the cyclical movement, such as mid-diastole, end-diastole, etc. Since the movement signal is obtained by a completely different mechanism than an ECG signal, the movement signal does not have the distinctive R-wave, which may easily be used as trigger point. Rather, the movement signal is to be analyzed to determine the physiological phases. However, this may not be done retrospectively if the movement signal is to be used in real-time applications for triggering. Therefore, in one or more of the present embodiments, the filter already applies a segmentation (e.g., a model-based segmentation). "Segmentation" provides that the physiological phases (e.g., such as diastole, systole) are assigned to the corresponding portions of the movement signal.

In one or more of the present embodiments, the filter not only denoises the movement signal, but already assigns segments or specific points of the movement signal to the respective phases of the movement signal (e.g., the cardiac component).

In one embodiment, the adaptive or stochastic or model-based filter is first trained or adapted to the selected independent component (e.g., the cardiac component, such as the cardiac component derived from the calibration portion). Thus, the calibration portion of the pilot tone signal may be used also to configure the filter, since the filter may during this training phase generate or adapt a model of the movement signal to the actual pilot tone signal acquired in that particular scan.

In other words, segmentation of the cardiac component enables triggering (e.g., on the start/end of distinct cardiac phases), but often relies on an a priori model of the cardiac cycle in either the time and/or frequency domain. In addition, model based segmentation is robust against measurement noise and may enable triggering on any, arbitrary points in the cardiac cycle. In the absence of severe arrhythmia, model based methods may also be able to predict cardiac activity beyond the current state. Therefore, model-based or stochastic filters may be applied to the movement signal.

In one embodiment, the filter is a Kalman Filter, or an Extended Kalman filter, or is a Switched/Switching Kalman Filter, where the Switching Kalman Filter switches between several models during various phases of the cyclical movement. Kalman filtering, also known as linear quadratic estimation (LQE), is an algorithm that uses a series of measurements observed over time, containing statistical noise and other inaccuracies, and produces estimates of unknown variables that tend to be more accurate than those based on a single measurement alone, by using Bayesian inference and estimating a joint probability distribution over the variables for each timeframe. Thus, the Kalman filter provides, based on the past measurements (e.g., the calibration portion), for each filtered data point, a probably correct data point. The Switched Kalman filter may also include information on the physiological phase of the data point (e.g., may already perform segmentation). The Kalman, Extended Kalman, and Switched/Switching Kalman filter make use of prior information trained on actual data. Thus, these and other model-based filters make use of a model of the movement signal.

Once such a model has been generated (e.g., by analysis of the cardiac component trace acquired during the calibration phase), segmentation may be achieved by various methods, such as Hidden Markov Models or Switched Kalman Filters. These methods may also be used retrospectively to obtain segmentations of the cardiac component.

The underlying model for implementations using the Kalman Filter/Smoother (e.g., extended) may be generated either in the frequency and/or time domain. Thus, the adaptive, stochastic, or model-based filter may be trained to the selected independent component in the frequency and/or in the time domain.

In the frequency domain, a possible model may be generated by analyzing the spectrum of the cardiac component acquired in the processing act, or on the movement signal or the cardiac component from the calibration portion of the Pilot Tone signal. The cardiac component is only quasiperiodic, especially in patients with arrhythmias; thus, each frequency component (e.g., amplitude and phase) may be modelled and tracked as a function of time. Several algorithms exist to implement the multiharmonic frequency-tracking Extended Kalman Filter (EKF)/Smoother (e.g., described in Kim, S., Paul, A. S., Wan, E. A., & Mcnames, J., Multiharmonic Frequency Tracking Method Using The Sigma-Point Kalman Smoother, EURASIP Journal on Advances in Signal Processing, 2010). Usually, up to three harmonics to the base heart rate may be resolved, and amplitude and phase information may be extracted. Using Fourier-synthesis, a time-domain model may then be calculated and fed to an Extended Kalman Filter.

Thus, in one or more of the present embodiments, the adaptive, stochastic, or model-based filter is based on up to three harmonics of the base rate of the cyclic movement (e.g., the cardiac movement).

Where the model is generated in the time domain, in a first embodiment, a time-domain model may be constructed based on biomechanical data of the heart. An Extended Kalman Filter then continuously fits incoming date from the cardiac component to this model. Using this approach, the Extended Kalman Filter is able to track at least some changes in heart frequency. Alternatively, in patients with severe arrhythmia, a plurality of models may be trained and switched depending on the incoming data.

In another embodiment, the time-domain representation of the cardiac component relating to one cardiac cycle (e.g., acquired during the calibration portion) may be decomposed into a plurality of segments. A time-domain model may then be constructed as a piecewise function serving as the basis for either Hidden-Markov based methods or a Switched Kalman Filter. The choice of segments may be arbitrary, or based on the underlying physiology.

In some embodiment, the adaptive or stochastic or model-based filter uses a model that incorporates physiological information about the cyclic movement (e.g., cardiac movement). Thus, the model may be based on a pre-configured model, which may, however, be adapted to the actual movement signal received during the scan of medical data. Thus, in an embodiment, the adaptive, stochastic, or model-based filter uses a Hidden Markov Model (HMM) or Switched Kalman filter (SKF). The Switched Kalman filter may be seen as an extension to the Hidden Markov Model.

In order to use the movement signal for triggering or post-processing the data acquired during the scan of medical data, the filtered movement signal may be segmented into two or more sections corresponding to two or more physiological phases of the cyclical movement. For example, the movement of a heart is segmented into diastolic phase and systolic phase, which repeat constantly. By segmentation, sections may be extracted from the filtered movement signal to describe physiological phases of the cyclical movement of a body part.

As described above, in one or more of the present embodiments, the adaptive, stochastic, or model-based filter automatically segments the movement signal into two or more sections corresponding to two or more physiological phases of the cyclical movement (e.g., to the phases of the cardiac movement such as systole and diastole). "Automatically segments" provides that the segmentation of the movement signals is performed without user input and may be done by the filter operation. Thus, the filter may identify sections or points of interest of the movement signal of the cyclical movement and allocates the physiological phases of the cyclical movement to the identified sections or points of interest.

In one embodiment, to generate delay-free triggering points, advanced filters are implemented (e.g., adaptive filters such as least mean squares (LMS), or the extended Kalman filter/smoother, HMM, or SKF). The least mean squares filter uses any form of a stochastic gradient descent method.

In alternative embodiments, where no HMM or SKF or similar advanced filter is applied, the first and/or second derivative of the filtered movement signal may be calculated and, for example, analyzed to extract time points used for triggering or post-processing. In this case, a filter that at least denoises or smoothes the movement signal representing the particular movement type is applied.

Accordingly, in one or more of the present embodiments, the time points used for triggering a scan of medical data from the part of the human or animal body, or for post-processing a scan of medical data performed during the acquisition of the pilot tone signal, are extracted from the filtered movement signal. In one embodiment, the time points are based on properties of the curve or on parameters of the stochastic, adaptive, or model-based filter. In one or more of the present embodiments, the time points used for triggering or post-processing may be directly derived from the stochastic, adaptive, or model-based filter, once the stochastic, adaptive, or model-based filter has been trained. For example, the time points may be related to the switching times of a Switched Kalman Filter, or the time points may be derivable from the model/template underlying the filter. In other embodiments, the time points used for triggering may be derived from analyzing the cardiac component (e.g., smoothed cardiac component; detecting minima, maxima etc.), possibly also in the first and/or second derivative, and explained in more detail below.

The time points used for triggering may be used in the same scan of medical data in which the time points have been acquired. For example, a calibration portion of the pilot tone signal is acquired, and a selection of triggering points is made (e.g., by a user). Then, the scan of medical data (e.g., MR-scan) starts using the selected triggering time points, which may be optimized to the objective of the MR-scan.

Possible useful trigger points are, for example, max(abs (1st derivative))=max velocity, or max(abs(2nd derivative)) =max acceleration or the minimum/maximum of the cardiac component trace. These points are easily obtained from the smoothed cardiac component trace and correspond to interesting features in the cardiac cycle like the early systolic and diastolic motion phases. Trigger points approximating the ECGs R-peak may be obtained by threshold based triggering using the mid-diastolic amplitude as an indicator.

In one embodiment, the acts of applying the demixing matrix and/or applying the adaptive or stochastic or model-based filter are performed such that no delay is introduced between the filtered movement signal and any further signal (e.g., a signal comprising magnetic resonance data), acquired at the same time as the pilot tone signal from the body part.

The term "no delay" provides that the delay may be kept to a minimum (e.g., between 0-10 ms or less than 1 ms), so that the filtered movement signal is effectively generated in real time. Thus, the filtered movement signal may be used for triggering a scan of medical data (e.g., an MR examination of the moving part of the human or animal body, such as the heart).

When no real-time functionality is to be provided, simple forward-backward filtering using either FIR or IIR digital filters in the time-domain or frequency-domain filtering on the cardiac component is sufficient to generate a filtered movement signal (e.g., "trace") on which feature detection algorithms (e.g., the above-described adaptive or stochastic or model-based filters) may be applied. "Forward-backward filtering" is a filter method that provides that the filtered movement signal is not shifted in time by the filter, so there is no delay between the images acquired during the scan of medical image data and the movement signal derived from the Pilot Tone signal (e.g., even if the images are not processed in real time). Since the filter does not have to operate in real time, filters of significantly higher order and with a lower cutoff-frequency may be used while maintaining zero delay through forward-backward filtering. This also effectively doubles the filter order. Alternatively, zero lag filtering in the frequency domain may be applied. The filter may serve to denoise/smooth the movement signal.

Accordingly, in an embodiment, instead of the stochastic or model-based filter, forward-backward filtering using, for example, FIR or IIR digital filters is performed on the movement signal.

Prior to the calculation of the demixing matrix, the pilot tone signal may be (pre-) processed, as described in the following.

In order to reduce noise, the PT signal may optionally be down-sampled to a new sampling frequency that is sufficient to capture cardiac dynamics (e.g., to 50 to 300 Hz; 180 Hz). This frequency is chosen so that the delay introduced by filtering during down-sampling is not too long. The choice of down-sampling rate is dependent on the image acquisition rate. For cardiac imaging, a sampling frequency of around 250-400 Hz is typical. Thus, in one embodiment, the pilot tone signal is down-sampled prior to the calculation of the demixing matrix and/or prior to the application of the demixing matrix to the further portions of the Pilot Tone signal To avoid aliasing of high-frequency noise, the signal may be low pass filtered prior to down sampling. For real-time triggering applications, the down sampling factor and filter order are limited by the maximum acceptable trigger delay. In this case, the new sampling rate is still to be sufficient to provide precise triggering, and the delay introduced by digital filtering (e.g., FIR or IIR structure) is to be low.

Instead of low pass filters, band pass filters may be used to suppress the respiratory signal as well, reducing the expected number of independent components.

A reasonable frequency range for heart rate in adult humans is about 0.8 Hz-3 Hz. In the cardiac component signal, usually the first and in some cases the second harmonic may be observed; therefore, an upper cut-off frequency of about 6-9 Hz is to be provided for the low pass or band pass filter. For retrospective applications, filters of significantly higher order and with a lower cutoff-frequency may be used.

Thus, in one embodiment, the pilot tone signal is low-pass filtered prior to the calculation of the demixing matrix and/or prior to the application of the demixing matrix to the further portions of the Pilot Tone signal In one or more of the present embodiments, the phases of all channels are then normalized to a reference phase of a selected channel, and only relative phase offsets to this reference are further considered. This removes potential phase drift and wrapping problems in some channels. Phase normalization is achieved by multiplying with the complex conjugate of the phase of the sample from the reference channel. The normalized complex navigator samples are then further processed to separate the motion components.

In order to reduce the complexity of the ICA problem, further pre-processing acts may be performed before the calculation of the demixing matrix, or before the ICA algorithm. These may include centering (e.g., subtracting the mean so that the resulting signals are zero-mean), whitening/sphering to provide that all signals have unit variance and are uncorrelated (e.g., for a given (n×m) matrix x, where n is the number of samples and m is the number of channels, Cov(x)=E{xxT}=I, with I the identity matrix), and dimensionality reduction.

Whitening may be achieved by principal component analysis (PCA) based on either eigenvalue or singular value decomposition. Dimensionality reduction may be performed by using only the k largest principal components/singular values, where k is smaller than the number of channels.

Thus, in one or more of the present embodiments, the method includes performing Principal Component Analysis (PCA) on the calibration portion of the Pilot Tone signal prior to the calculation of the demixing matrix. This may be done in order to whiten the signal components of the pilot tone signals, where the whitened components of the pilot tone signal have unit variance. In one embodiment, the PCA is performed prior to ICA (e.g., a PCA) is first performed on all the signal components of the pilot tone signal. Thereby, the principal/orthogonal components may be identified, which leads to a reduction in dimensionality. For example, from the original 64 signal components corresponding to the channels, PCA may derive a reduced number (e.g. 20) of principal components. Thus, the PCA is used as a pre-stage to the ICA, to create a reduced number of channels. The ICA is then performed on the reduced number of channels.

In one embodiment, the method provides an act of displaying the filtered movement signal, for example, together with information on the physiological phases and/or time points within the cyclical movement. Thus, the filtered movement signal is rendered as a graph of signal intensity over time for one or several heartbeats, and shown on, for example, a computer display in a form that a user may monitor the cardiac movement, and may thus check whether the parameters of the scan of medical image data are to be adjusted.

For monitoring purposes, the delay introduced by higher order digital filters is negligible. Hence, fast visual feedback of the filtered movement signal (e.g., the cardiac component trace) may be provided to the user in an online display. The incoming raw data may be bandpass filtered to remove both noise and any remnants of the respiratory component still present in the calculated cardiac component.

If model based segmentation of the cardiac trace is available, in addition to displaying the real-time cardiac component trace, a single and/or average cardiac cycle may be displayed in a user interface together with the segmented physiological phases or time points. Possible methods for visualization have been detailed in DE 10 2015 224 162 A1 and are incorporated herein by reference.

Thus, one or more of the present embodiments provide a method to visualize the cardiac component trace in real-time, for quality check, and patient supervision. In one or more of the present embodiments, this is done by bandpass-filtering the cardiac component and displaying the cardiac component in a suitable image update rate (e.g., displaying 3-8 cardiac cycles in a row and overwriting on a rolling base).

The cardiac component trace may also be encoded in the DICOM data (e.g., as an image overlay and/or as grayscale image content) for further post processing. Alternatively, in the new DICOM format, the cardiac component trace may be saved as a 1D signal. The triggers may also be stored in this way.

In one embodiment, the movement signal or the filtered movement signal is provided and may be saved in a computer-readable file. This file may be stored on a digital storage medium. The movement signal or the filtered movement signal may also sent over the Internet and used/stored elsewhere.

In some embodiments, the filtered movement signal includes further features (e.g., information on the position of important time points within the cyclical movement). Further features may help a user or the method to find characteristic points in the cyclical movement (e.g., the onset of systole of the heart).

The filtered movement signal is derived from and/or directly describes the mechanical activity of the moving part of the human or animal body. Thus, the filtered movement signal is not directly related to the electrical activity (e.g., the ECG), but has a more direct correspondence to the actual state of contraction of the heart.

One or more of the present embodiments are further directed to a computer program including program code that induces a computer to perform the method as described, when the program code is executed on the computer. The computer program may be started and ended by a user. A plurality of input parameters may be entered by a user to optimize the output of the method.

One or more of the present embodiments are further directed to a digital storage medium (e.g., a non-transitory computer-readable storage medium) including the program code (e.g., instructions), as described. The digital storage medium may be in form of a hard drive, like a magnetic hard disk or a solid state drive, or in form of a portable storage medium like a CD, DVD or USB-Stick, or in the form of a network storage medium, like a NAS-storage or a cloud storage.

One or more of the present embodiments are further directed to a control unit adapted for performing the method as described, where the control unit may be part of a computer and/or part of a magnetic resonance machine.

DETAILED DESCRIPTION

In the following and with reference to FIG. 1, an embodiment of a method is described. In the example, it is assumed that a pilot tone signal is acquired during a magnetic resonance (MR) scan. The processing of the acquired signal may include the following acts.

Calibration act: These acts may be the same as described in the DE 10 2015 224 162 A1. The purpose of the calibration act is to determine the frequency of the pilot tone signal and to separate the MR imaging signal from the additional Pilot Tone signal.

1) Pre-processing act: optionally down-sampling the pilot tone signal (including a plurality of signal components from the plurality of receiving coil channels) and optionally low-pass filtering or bandpass filtering to suppress unwanted signals, such as the respiratory signal, and normalizing the phases of all channels to a reference phase.

2) Processing act: Calculating the demixing matrix W separating the cardiac component by applying an independent component analysis (ICA) (e.g., from a short calibration scan), and applying the demixing matrix on incoming data.

4 a) Filtering/triggering act: For real-time applications, denoising of the cardiac component and feature detection to enable triggering on an arbitrarily positioned predefined point in the cardiac cycle.

4 b) Filtering/post-processing act: For retrospective applications, retrospective processing of the cardiac component and the feature extraction.

5) Visualization act: Optionally, real-time visualization of the filtered movement signal (e.g., the processed cardiac component).

Figure 1:
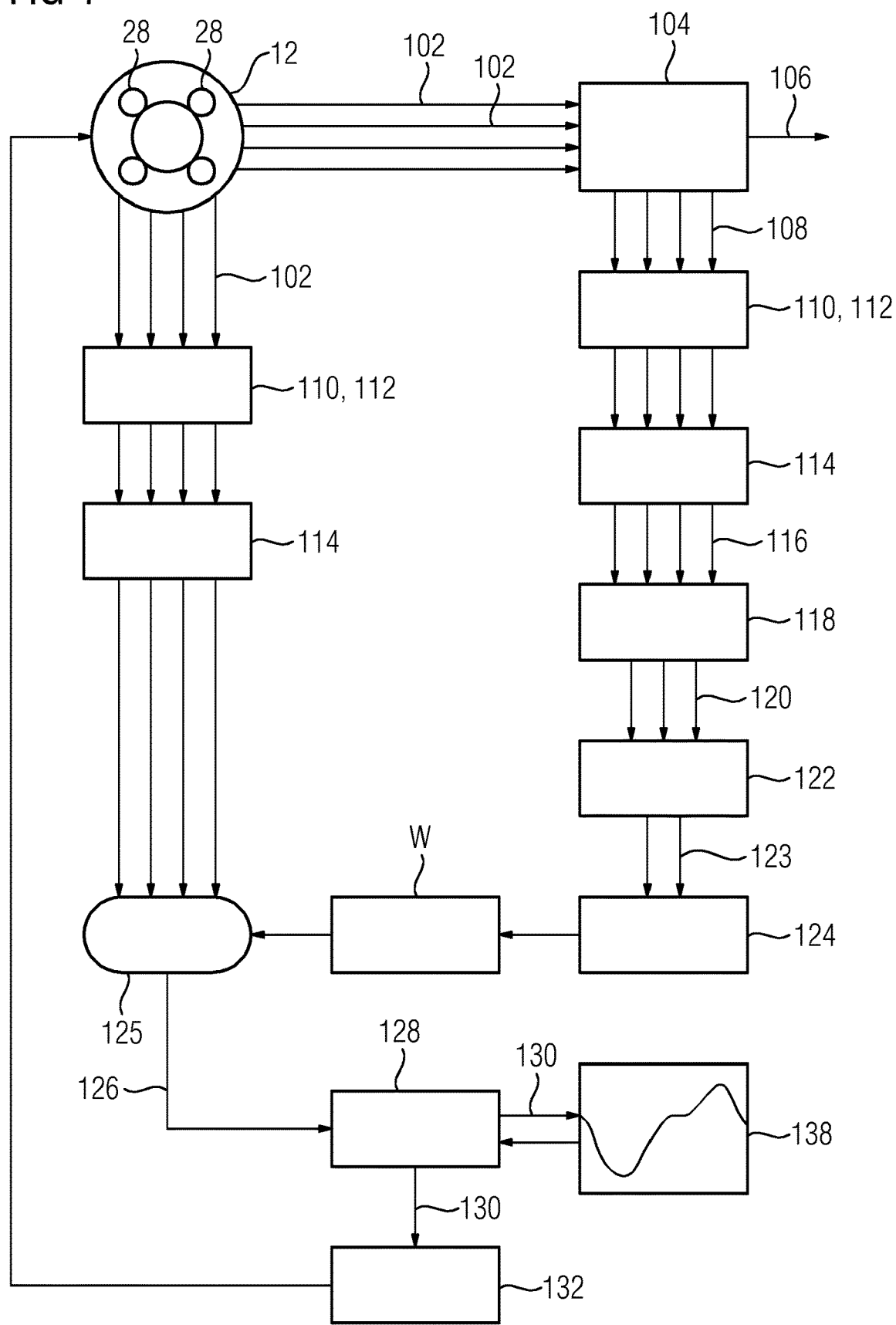
FIG. 1 shows a schematic flow diagram of an embodiment of a method.

A flow diagram of this method in more detail is shown in FIG. 1. The MR scanner 12 including a receiver coil arrangement 28 with, for example, four coils/channels is shown on the top left. When the acquisition starts, the receiver coil arrangement acquires a signal 102 having 4 signal components. The signal 102 is first subjected to a calibration act 104. In one or more of the present embodiments, the absolute frequency of the pilot tone signal is determined in this act and stored for use in further measurements. Optionally, a model for the expected complex navigator signal may be computed based on the calibrated absolute frequency and the knowledge of the receiver mixing frequency of the current scan/readout. The complex pilot tone (e.g., navigator) signal amplitude and phase may then be determined for each coil element by complex multiplication with the complex conjugated model. Then, the modelled Pilot Tone may be subtracted from the incoming MR signal 102 to obtain clean MR data 106. The MR data 106 is further processed to produce MR image data, as is known in the art.

The pilot tone signal 108 including the 4 signal components is optionally pre-processed by low-pass or bandpass filtering 110 (e.g., to avoid aliasing of high-frequency noise), followed by down-sampling 112. This is because the MR signal is acquired at a very high sampling rate, which is not required for the analysis of cardiac motion. The pre-processing in optional because the pre-processing increases signal to noise ratio (SNR) but at the cost of additional time delay.

The pre-processed signal is further subjected to a normalization act 114, in which the phases of all channels are normalized to a reference phase. The phase normalization may be achieved by multiplying with the complex conjugate of the reference channel (e.g., one of the channels is selected as the reference channel). The normalised, complex pilot tone signals 116 are then further processed to separate the various motion components modulating the Pilot Tone signal. This is done first by principle component analysis 118, in which the largest principle components 120 are extracted, as described above. Only the largest principle components are then subjected to independent component analysis 122. Through the ICA, the different components 123 of the pilot tone signals are separated. Typically, a further reduction in dimensionality occurs, as schematically indicated in the drawing (e.g., three components 120 are reduced to two components 123; for respiratory motion and cardiac motion). The selection of the cardiac component from the independent components 123 is done in act 124. The act 124 may be done automatically (e.g., by calculating the signal energy in the cardiac motion band for each independent component, compared to the signal energy in other frequency bands, and selecting the component with the highest relative signal energy in the cardiac motion band). Alternatively, the degree of correlation of each signal component with a typical cardiac component trace may be calculated. Once the correct independent component representing the cardiac motion has been selected, the demixing matrix W may be automatically calculated. The demixing matrix W may correspond to a linear combination of the signal components 102/116 of the several receiver channels.

The demixing matrix W is then stored and applied to the incoming further Pilot Tone signal data 102. In some applications, the incoming data 102 may first be subjected to low-pass filtering and down-sampling 110/112, as well as phase-normalization 114. The normalized complex samples are then multiplied with the demixing matrix W in act 125 to obtain the at least one selected independent component (e.g., the cardiac component 126). The signal representing the cardiac movement 126 (e.g., movement signal) is then subjected to a filter 128, as described above. In some embodiments, the filter is first trained on a calibration portion of the movement signal. The above-described adaptive filters like the Kalman Filters and Switched Kalman Filters need some time to converge; thus, a calibration is useful to provide fast convergence, but not absolutely necessary. In other applications, the filter 128 adapts over time to the incoming movement signal 126 and does not require a calibration.

Acts 104-124 may be carried out on a calibration portion of a pilot tone signal, which may be acquired prior to the MR acquisition or during a phase of the MR examination in which the parameters for the MR examination are selected by the operator, such as the field of view and the type of measurement. Thereby, the MR examination time is not prolonged by the determination of the demixing matrix.

The filtered movement signal 130 may then be visualized on a screen 38. This may be done continually, so that the user may monitor the patient's heart activity. Also, trigger points may be selected on a user-interface 38. From the filtered movement signal or filtered cardiac component 130, trigger points 132 may be extracted (e.g., this is done automatically by the filtering act 128). The trigger points 132 may be used in real-time for triggering the MR scan occurring in the MR scanner 12.

Figure 2:
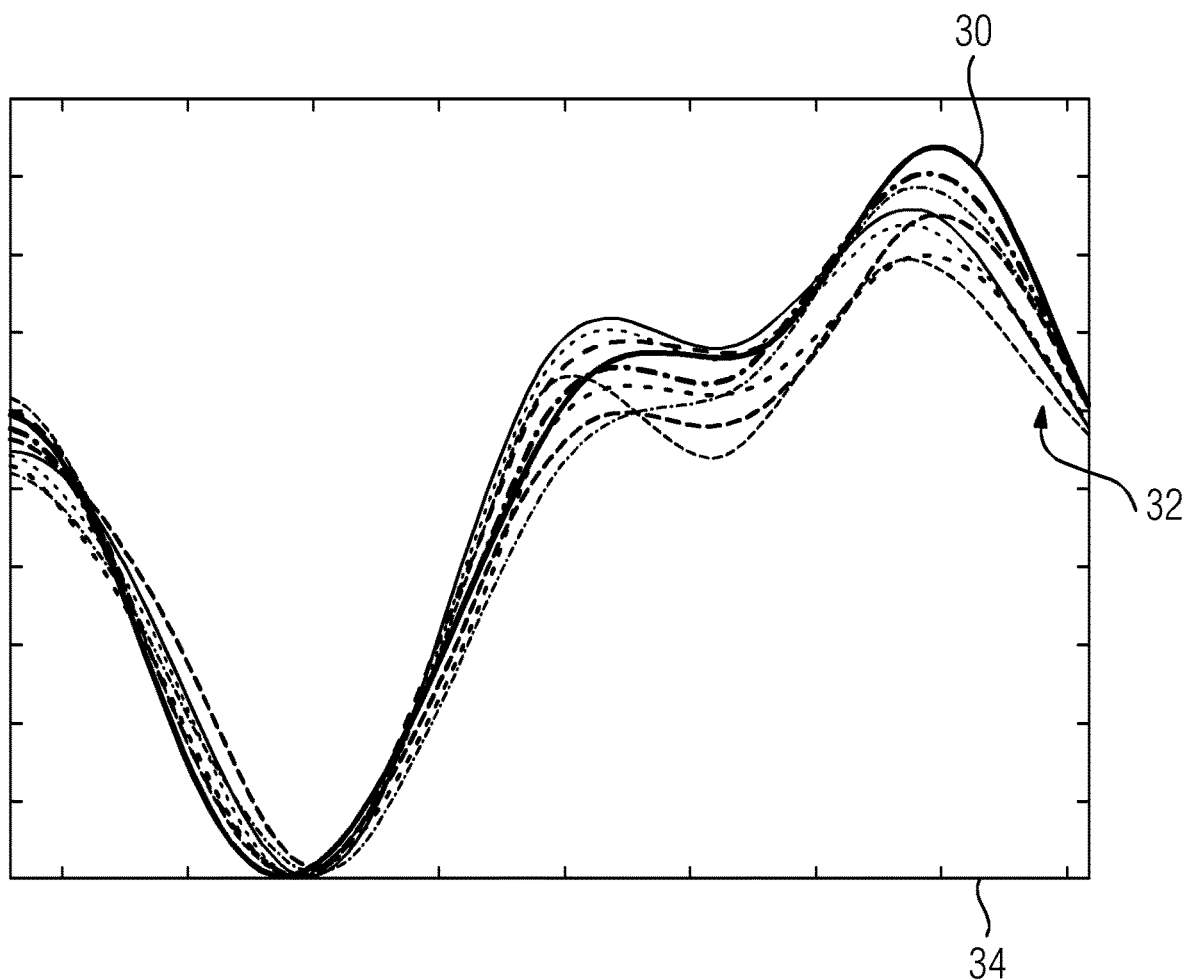
FIG. 2 shows an example of a plurality of signal components received by receive channels over a mean cardiac cycle (dashed lines) and the cardiac component selected therefrom by ICA (solid line).

FIG. 2 shows an example of the several signal components 32 (in dashed lines) averaged over several cardiac cycles, as well as the cardiac component extracted by ICA 30 in solid line. The signal intensity 36 is plotted versus time 34.

Figure 3:
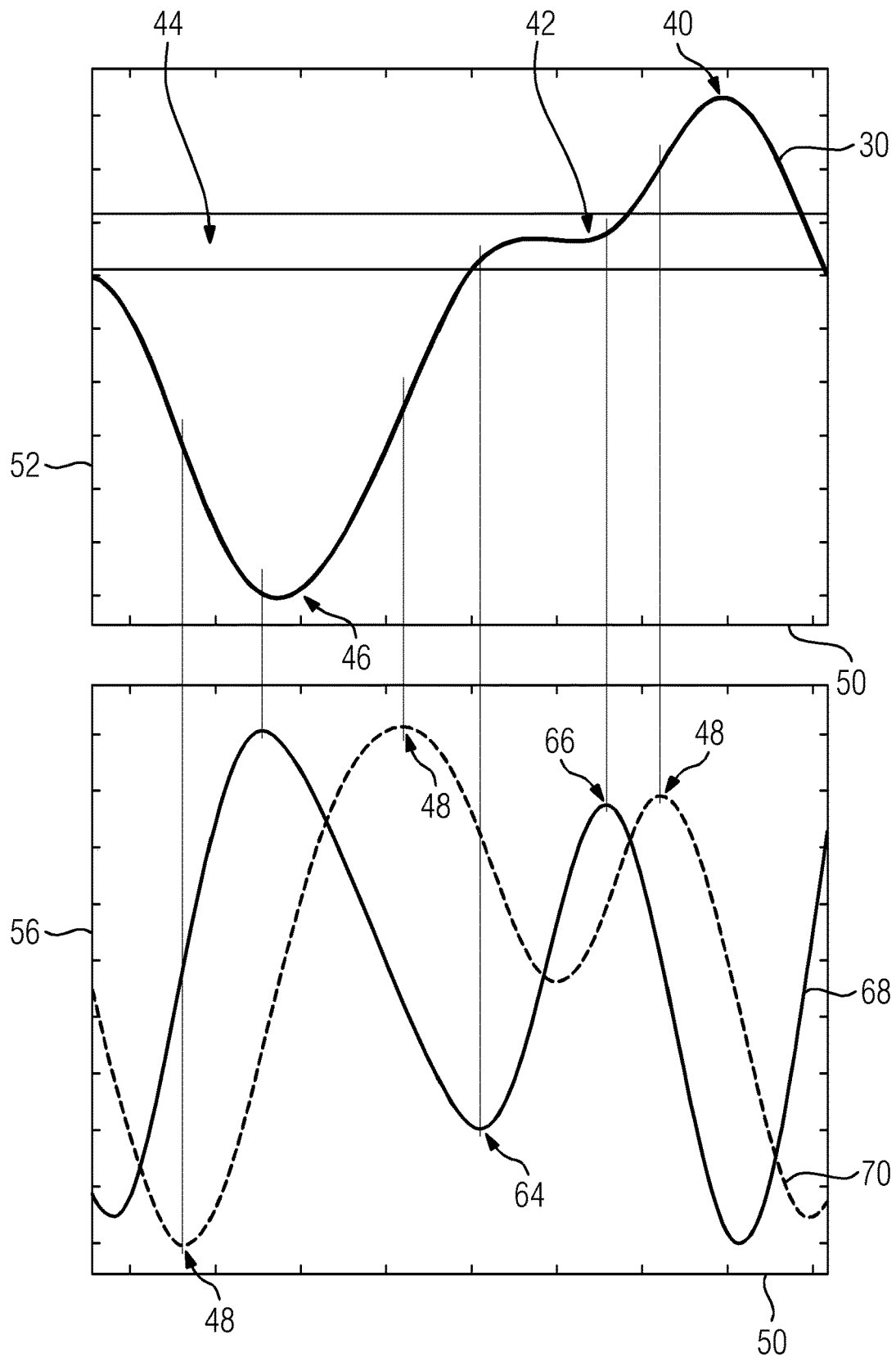
FIG. 3 shows an example of a cardiac component trace over one cardiac cycle, and corresponding first and second derivatives.

The cardiac component trace 30 is filtered, as described above (e.g., by a switched Kalman filter based on a model generated by analysis of the cardiac component trace acquired during the calibration phase). The filtered cardiac component trace 30 is shown again in the top graph of FIG. 3 in a plot of amplitude 52 in arbitrary units versus time 50. In the bottom part of the graph, the first derivative 70 (in dashed line) and second derivative 68 are also shown in arbitrary units 56 plotted against time 50. From the filtered cardiac component trace, the following points of interest may be derived: The minimum of the cardiac component trace 46 indicates end-systole (e.g., the maximum contraction and resting phase). The maximum of the cardiac component 40 indicates end-diastole (e.g., the physiological phase of maximum expansion of the heart during the resting phase). The plateau 42 may be associated with the mid-diastolic phase, in which the ventricle is relaxed (e.g., a resting phase). The area 44 indicates the signal level for R wave occurrence, and may be used in a threshold trigger. The minima 48 and maxima 48 of the first derivative 70 of the cardiac component indicate the times of maximum velocity. The minimum 64 and the maximum 66 of the second derivative 68 indicate the start and end of the mid-diastolic phase.

Figure 4:
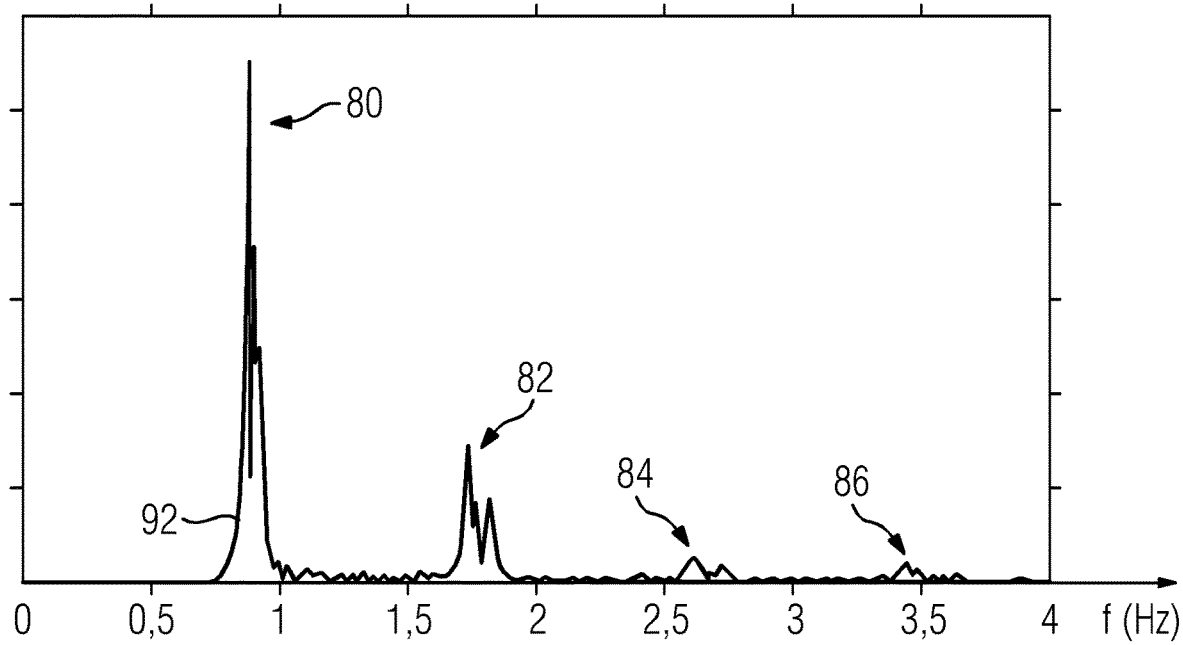
FIG. 4 shows a schematic spectral analysis of a band-pass filtered cardiac component trace (0.5 Hz-4 Hz).

FIG. 4 shows a spectral analysis of a band-pass filtered cardiac component trace in the frequency range of 0.5 to 4 Hz. The cardiac component 92 has a main peak 80 at the base frequency corresponding to the heart rate. The first harmonic 82, the second harmonic 84, and the third harmonic 86 may also be resolved, showing systole-diastole dynamics. The splitting and broadening of the peaks is due to varying heart rate during the 90 seconds acquisition. From the spectral analysis, amplitude and phase information may be extracted using Fourier synthesis; a time-domain model may then be calculated and fed to, for example, an extended Kalman filter.

Figure 5:
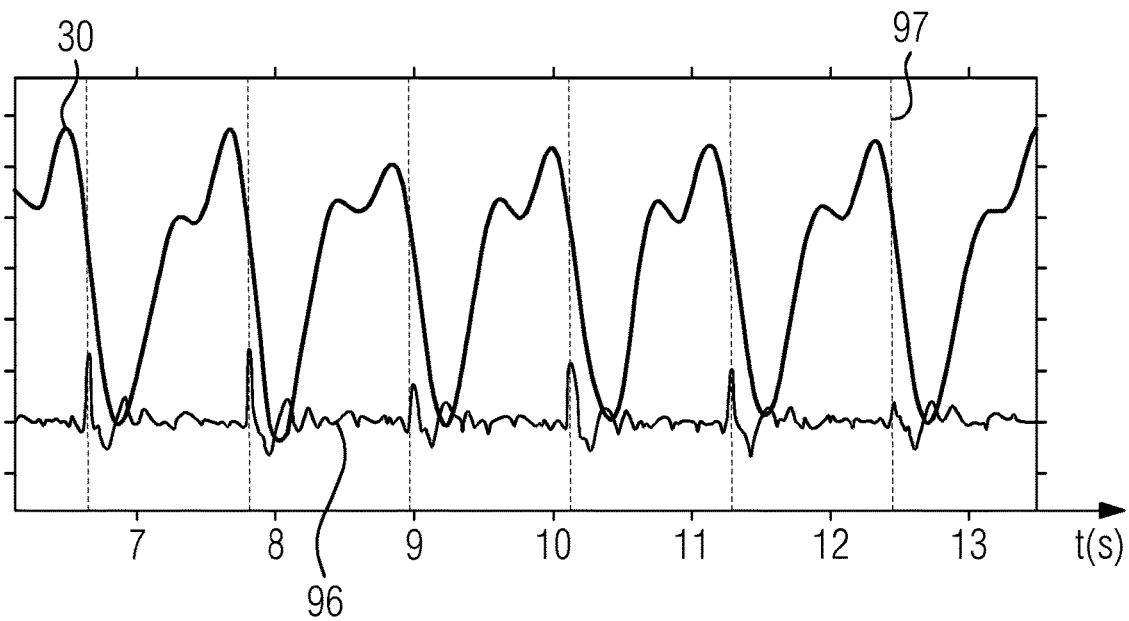
FIG. 5 shows a schematic Bandpass-filtered cardiac component trace and corresponding ECG trace, where triggers (vertical dashed lines) were extracted from the ECG.

FIG. 5 is an illustration of a possible visualization act. In FIG. 5, the cardiac component trace 30 is plotted over six cardiac cycles against time. The cardiac component trace is shown over a time span of about 7 seconds. The cardiac component trace 30 has been band-pass filtered before. A corresponding ECG trace 96 is also plotted, where the respective R waves are shown as dashed lines 97.

Figure 6:
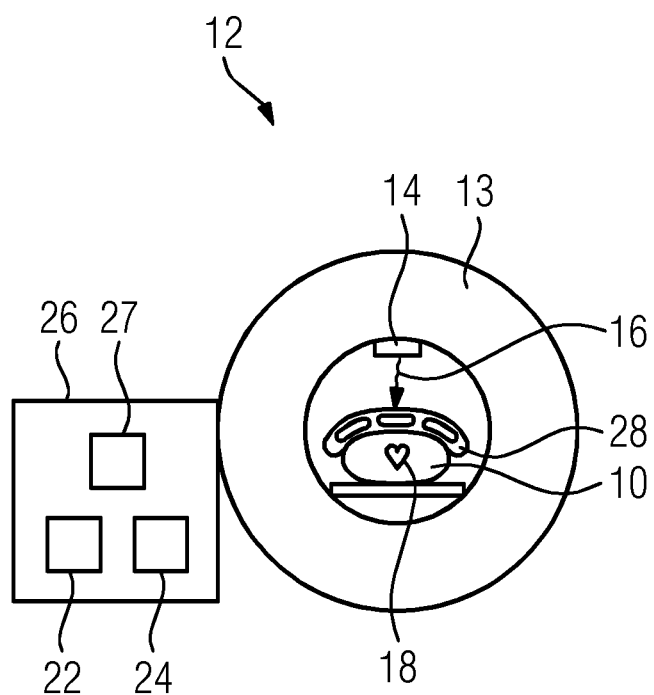
FIG. 6 shown one embodiment of a magnetic resonance (MR) scanner in a schematic view.

FIG. 6 shows a schematic MR scanner 12. The MR-scanner 12 includes a main magnet 13 and a control unit 24, by which the data acquisition of the MR scanner 12 may be controlled. The control unit 24 may be part of a computer device 26. The computer device may also include a digital storage medium 22 and a user interface 27 including, for example, a display, a keyboard, mouse, touch screen, or the like. A patient 10 may be examined, for example, in order to perform MR imaging of the heart 18.

In order to provide the movement signal, a pilot tone signal 16 is emitted by a pilot tone emitter 14 that may be a separate RF source. In one embodiment, the pilot tone emitter 14 is positioned close to the heart (e.g., strapped to the local coil 28 or included in the coil). The pilot tone signal is modulated by the movement of the heart 18 and the lung (not shown).

The pilot tone signal (e.g., modulated pilot tone signal) is received by the receiver coil arrangement 28, which may be a local coil 28, such as a head coil or chest array coil, but may also be the body coil.

The elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent. Such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A method for generating a movement signal of a part of a human or an animal body, of which at least a portion is undergoing a cyclical movement, the method comprising:
providing a Pilot Tone signal acquired from the body part by a magnetic resonance receiver coil arrangement, the magnetic resonance receiver coil arrangement comprising a plurality of channels, wherein the Pilot Tone signal is a frequency signal outside the receive bandwidth of a magnetic resonance scan of the body part, and wherein the Pilot Tone signal comprises a plurality of signal components associated with the plurality of channels;
calculating, from a calibration portion of the Pilot Tone signal, a demixing matrix by an independent component analysis (ICA) algorithm, wherein the demixing matrix calculates independent components from the plurality of signal components;
selecting the independent component corresponding to one particular movement type;
obtaining at least one movement signal representing one particular movement type, the obtaining of the at least one movement signal comprising applying the demixing matrix to further portions of the Pilot Tone signal; and
obtaining a filtered movement signal, the obtaining of the filtered movement signal comprising applying an adaptive, stochastic, or model-based filter to the at least one movement signal representing the one particular movement type.

2. The method of claim 1, wherein the filter is an adaptive, stochastic, or model-based filter.

3. The method of claim 2, further comprising training or adapting the adaptive, stochastic, or model-based filter to the selected independent component.

4. The method of claim 3, wherein training or adapting the adaptive, stochastic, or model-based filter to the selected independent component comprises training or adapting the adaptive, stochastic, or model-based filter to the independent component from the calibration portion.

5. The method of claim 2, wherein the adaptive, stochastic, or model-based filter is a Kalman Filter, an Extended Kalman filter, or a Switched Kalman Filter that switches between a plurality of models during various phases of the cyclical movement.

6. The method of claim 2, wherein the adaptive, stochastic, or model-based filter uses a Hidden Markov Model.

7. The method of claim 2, wherein the adaptive, stochastic, or model-based filter is trained to the selected independent component in a frequency, in a time domain, or in the frequency and the time domain.

8. The method of claim 2, wherein the adaptive, stochastic, or model-based filter automatically segments the movement signal into two or more sections corresponding to two or more physiological phases of the cyclical movement.

9. The method of claim 8, wherein the adaptive, stochastic, or model-based filter automatically segments the movement signal into two or more sections corresponding to phases of the cardiac movement.

10. The method of claim 9, wherein the phases of the cardiac movement comprise systole and diastole phases.

11. The method of claim 1, wherein the applying of the filter comprises forward-backward filtering the movement signal.

12. The method of claim 11, wherein the filter is a finite impulse response (FIR) digital filter or an infinite impulse response (IIR) digital filter.

13. The method of claim 2, wherein the applying of the demixing matrix, the applying of the adaptive, stochastic, or model-based filter, or the applying of the demixing matrix and the applying of the adaptive, stochastic, or model-based filter are performed such that no delay is introduced between the filtered movement signal and any further signal.

14. The method of claim 13, wherein the applying of the demixing matrix, the applying of the adaptive, stochastic, or model-based filter, or the applying of the demixing matrix and the applying of the adaptive, stochastic, or model-based filter are performed such that no delay is
introduced between the filtered movement signal and a signal comprising magnetic resonance data, acquired at a same time as the Pilot Tone signal from the body part.

15. The method of claim 2, further comprising extracting time points used for triggering a scan of medical data from the part of the human or the animal body, or for post-processing a scan of medical data performed during the acquisition of the Pilot Tone signal from the filtered movement signal.

16. The method of claim 15, wherein extracting the time points comprises extracting the time points from the filtered movement signal based on properties of a curve or parameters of the adaptive, stochastic, or model-based filter.

17. The method of claim 1, further comprising performing principal component analysis on the calibration portion of the Pilot Tone signal prior to the calculation of the demixing matrix, in order to whiten the signal components of the Pilot Tone signals,
wherein the whitened components of the pilot signal have unit variance.

18. The method of claim 1, wherein prior to the calculation of the demixing matrix, prior to the application of the demixing matrix to the further portions of the Pilot Tone signal, or prior to the calculation of the demixing matrix and prior to the application of the demixing matrix to the further portions of the Pilot Tone signal, the Pilot Tone signal is down sampled, low-pass filtered, or down sampled and low-pass filtered.

19. The method of claim 1, wherein the filtered movement signal is derived from, directly describes, or is derived from and directly describes a mechanical activity of the moving part of the human or animal the body.

20. A non-transitory computer-readable storage medium storing instructions executable by one or more processors to generate a movement signal of a part of a human or an animal body, of which at least a portion is undergoing a cyclical movement, the instructions comprising:

providing a Pilot Tone signal acquired from the body part by a magnetic resonance receiver coil arrangement, the magnetic resonance receiver coil arrangement comprising a plurality of channels, wherein the Pilot Tone signal is a frequency signal outside the receive bandwidth of a magnetic resonance scan of the body part, and wherein the Pilot Tone signal comprises a plurality of signal components associated with the plurality of channels;

calculating, from a calibration portion of the Pilot Tone signal, a demixing matrix by an independent component analysis (ICA) algorithm, wherein the demixing matrix calculates independent components from the plurality of signal components;

selecting the independent component corresponding to one particular movement type;

obtaining at least one movement signal representing one particular movement type, the obtaining of the at least one movement signal comprising applying the demixing matrix to further portions of the Pilot Tone signal; and obtaining a filtered movement signal, the obtaining of the filtered movement signal comprising applying an adaptive, stochastic, or model-based filter to the at least one movement signal representing the one particular movement type.

\* \* \* \* \*